United States Patent
Backus (10) Patent No.: US 10,123,132 B2
(45) Date of Patent: Nov. 6, 2018

(54) STIMULATION STRATEGY FOR AN AUDITORY DEVICE COMPRISING AN ELECTRODE ARRAY

(71) Applicant: OTICON MEDICAL A/S, Smørum (DK)

(72) Inventor: Bradford Backus, Vallauris (FR)

(73) Assignee: Oticon Medical A/S, Smørum (DK)

( * ) Notice: Subject to any disclaimer, the term of this patent is extended or adjusted under 35 U.S.C. 154(b) by 52 days.

(21) Appl. No.: 15/054,911

(22) Filed: Feb. 26, 2016

(65) Prior Publication Data

US 2016/0255443 A1   Sep. 1, 2016

(30) Foreign Application Priority Data

Feb. 27, 2015 (EP) .................................. 15156861

(51) Int. Cl.
*H04R 25/00* (2006.01)
*A61N 1/05* (2006.01)
*A61N 1/36* (2006.01)

(52) U.S. Cl.
CPC ......... *H04R 25/356* (2013.01); *A61N 1/0541* (2013.01); *A61N 1/36032* (2013.01); *H04R 25/505* (2013.01); *H04R 25/552* (2013.01); *H04R 2225/43* (2013.01); *H04R 2225/67* (2013.01)

(58) Field of Classification Search
CPC combination set(s) only.
See application file for complete search history.

(56) References Cited

U.S. PATENT DOCUMENTS

| | | | |
|---|---|---|---|
| 9,283,376 B2* | 3/2016 | Wouters | A61N 1/36036 |
| 2004/0172101 A1 | 9/2004 | Van Hoesel | |
| 2005/0008177 A1* | 1/2005 | Ibrahim | H04R 25/30 381/316 |
| 2012/0004706 A1* | 1/2012 | Meister | A61N 1/36032 607/57 |
| 2012/0303093 A1 | 11/2012 | Wouters et al. | |
| 2015/0265837 A1* | 9/2015 | Kulkarni | H04R 25/407 381/313 |

* cited by examiner

*Primary Examiner* — Amir Etesam
(74) *Attorney, Agent, or Firm* — Birch, Stewart, Kolasch & Birch, LLP (57) ABSTRACT

According to an embodiment, an auditory device for generating an electrode stimulation signal is disclosed. The device includes a filter bank configured to filter an incoming audio signal into a plurality of band pass limited audio signals, each band pass limited audio signal relating to an audio frequency band. The device further includes a processor configured to extract an onset time for firing an electrode in accordance with rate of change of a band pass limited audio signal and/or a derived band pass limited audio signal satisfying a predetermined criterion, and a signal generator for generating the electrode stimulation signal for the electrode corresponding to the band pass limited audio signal and/or derived band pass limited audio signal in accordance with the determined onset time. The device includes a plurality of implantable stimulation electrodes configured to deliver the electrode stimulation signal to a region of cochlea.

18 Claims, 7 Drawing Sheets

STIMULATION STRATEGY FOR AN AUDITORY DEVICE COMPRISING AN ELECTRODE ARRAY

FIELD

The disclosure relates to an auditory device comprising an electrode array, for example a cochlear implant system including an implanted electrode array. In particular, the disclosure relates to a sound processing strategy employed in conjunction with such devices.

BACKGROUND

Cochlear implants are implantable systems, which can provide hearing to profoundly deaf or severely hearing impaired persons. Unlike conventional hearing aids that mechanically apply an amplified sound signal to the middle ear, a cochlear implant provides direct electrical stimulation to multiple implanted electrodes that excite the acoustic nerve in the inner ear, thus giving a sensation of hearing.

While cochlear implants improve the quality of life for many people worldwide, electric hearing still lacks the resolving ability found in normal hearing. Electrical hearing is not equivalent to normal hearing because the activation of the auditory nerve by cochlear implant electrode currents is not faithful to the pattern produced by normal physiological mechanisms. Notably, electric stimulation lacks the spatial and temporal resolution of normal hearing mechanism, reasons that are known to degrade ability of CI users to understand speech in noisy environment and to localize sound.

Most current cochlear implants use speech coding strategies that encode acoustic signals into electrical pulses for stimulating the acoustic nerve. One common speech coding strategy is the so called "continuous-interleaved-sampling strategy" (CIS). The CIS speech coding strategy samples the signal envelope within individual frequency bands at predetermined time intervals, providing an increased level of speech understanding merely by coding the amplitude modulation (AM) of the speech signal in each band. Each electrode is stimulated with an intensity corresponding to the instantaneous amplitude of the corresponding filter channel. In this strategy, the analysis period is predetermined and hence the frequency of stimulation for each electrode is more or less fixed.

Another coding strategy—Fine Structure Processing (FSP) analyzes the phase of the band pass signals and synchronizes the stimulation pulses with specific events in the phase of the corresponding electrode. In FSP coding, time events are defined using the zero crossings of the band pass signal where all channels are stimulated sequentially in a predetermined order. Other approaches providing some temporal fine structure information include—Peak Derived Timing (PDT) coding that derives the timing of stimulation pulses from the positive peaks in the band pass signals. Spike-based Temporal Auditory Representation (STAR) strategy extracted the pulse timing from the zero crossings of the band pass signals.

It is accepted that listening with two ears rather than one, for normal listeners, allows improved speech intelligibility in noise as well as the ability to better determine sound direction. Studies with both normal hearing and hearing impaired listeners has shown significant enhancement in performance during diochotic (different sounds in two ears) listening when compared to diotic (same sounds in two ears) listening. The improvement can be measured as a binaural intelligibility level difference (BILD), defining the difference in signal level between two binaural conditions for a given percent intelligibility. The enhancement is known to be a function of both interaural level differences cues (ILDs) and interaural time difference cues (ITDs). Similarly, localisation in the horizontal plane has been shown to be a function dependent on these ILD and ITD cues.

The disclosure offers an alternative to current coding techniques—a stimulation strategy that may better mimic the neural firing patterns of a healthy cochlea in order to present stimulation pulses at more physiologically proper times and locations in the cochlear implant. Thus, a method and system of processing sound waves into electrical signals that capture Fine Time Structure (FTS) information in incoming sounds and accurately direct this information to appropriate nerves that spatially innervate the cochlea is presented.

SUMMARY

The disclosure discusses auditory device with a focus on cochlear implant for illustrative purposes. It is to be understood that the disclosed stimulation strategy may equally apply for brain stem implant or modiolar implants and other auditory neurostimualors.

According to an embodiment, an auditory device for generating an electrode stimulation signal is disclosed. The device includes a filter bank configured to filter an incoming audio signal into a plurality of band pass limited audio signals, each band pass limited audio signal relating to an audio frequency band. The device further includes a processor configured to extract an onset time for firing an electrode in accordance with rate of change of a band pass limited audio signal and/or a derived band pass limited audio signal satisfying a predetermined criterion, and a signal generator for generating the electrode stimulation signal for the electrode corresponding to the band pass limited audio signal and/or derived band pass limited audio signal in accordance with the onset time. Lastly, the device further includes a plurality of implantable stimulation electrodes configured to deliver the electrode stimulation signal to a region of cochlea.

In an embodiment, the device includes a microphone that is adapted to receive the sound signal from user's environment. The microphone is adapted to generate the incoming audio signal based on the received sound signal. In some embodiment, the microphone may include a microphone array, e.g. for providing direction-dependent audio signal processing in different beamforming modes. Beamforming involves processing audio signals received at the microphones of the array in such a way as to make the array act as a highly directional microphone.

The filter bank, configured to receive the incoming signal, includes an array of frequency specific signal filters that separates the incoming audio signal, such as speech or music, into the plurality of band pass limited audio signals. Typically, the filter bank has a number of narrow frequency band filters with each filter associated with a specific band of audio frequencies. The incoming audio signal is thus filtered into the plurality of band pass limited audio signals where each signal corresponds to the band of frequencies for one of the band pass filters.

The electrode stimulation signal includes a signal that is used to generate an electric pulse. The generated electric pulse is provided to the implanted electrode, which sends impulses by way of the auditory nerve to the brain, which recognizes the signals as sound. The electrode stimulation signal is frequency band specific and are associated with a particular electrode of an electrode array. Each electrode of the plurality of electrodes include a different frequency distribution as defined by a corresponding audio frequency range. For example, the electrode array may include 20 implanted electrodes where electrode 1 close to the base of the cochlea associated with a frequency range between 6800 Hz to 8000 Hz, electrode 2 associated with a frequency range between 5800 Hz to 6800 Hz and so on with electrode 20 being closest to the apical region and covering frequency range between say 200 Hz to 300 Hz. It is apparent that the electrode array may include less or more than 20 electrodes and the frequency distribution for the electrodes may vary. The electrodes corresponding to the associated frequency range are frequency-place matched along length of the cochlea such that an electric pulse carrying information of a specific frequency band activates the corresponding electrode, as defined by the assigned frequency range, and in effect a specific frequency region of the auditory nerve along the cochlea.

As explained in the preceding paragraph, each electrode of the electrode array are associated with a specific frequency range. Therefore, the electrode 'corresponding' to the band pass limited audio signal and the derived band pass limited audio signal refers to electrode that is assigned with frequency included in the frequency band of the (derived) band pass limited signal. It is understandable that the number of frequency bands and the audio frequency ranges may be same or different. It is also apparent that the more than one frequency range is covered within a single frequency band or vice versa.

The onset time defines when to fire the electrode. In broad terms, the onset time forms the basis for the proposed sound processing (coding) strategy in which the time of stimulus (onset time) for a given electrode is synchronized or substantially synchronized to the rate of change of the filter output corresponding to that electrode. The filter output include the band pass limited audio signal or post envelope generation, the derived band pass limited audio signal as well. As a consequence, the timing information for the corresponding sound signal is also presented to the user.

In essence, the disclosure focuses on determining the onset time when the rate of the change satisfies a predetermined criterion in the band pass limited audio signal or the derived band pass limited audio signal of the incoming audio signal to dictate when the stimulation is to be applied to the cochlea. By focusing on the predetermined criterion, the onset time reflects the results of psychophysical tests on normal hearing individuals. Thus, the rate of change, in particular when slope of the is maximum for the band pass limited audio signal and/or a derived band pass limited audio signal, based on the disclosed onset time better mimics natural neural firing patterns of a healthy cochlea in order to present stimulation pulses at proper times (as defined by the onset time) and locations in the cochlea (as defined by place matching of the electrode within the cochlea). This allows for the temporal information in the incoming audio signal to be better preserved and providing the user with improved real time stimulation.

The band pass limited audio signals may be decomposed into an envelope of a signal that is broadly defined as the slow changes in time of the signal and the fine time structure that are the fast changes in time, i.e. the carrier wave(s) of the signal. The device include an envelope generator configured to generate a signal envelope for the band pass limited audio signal, the signal envelope defining the derived band pass limited audio signal. The envelope generator may compute the signal envelope based on a Hilbert transformation, and/or based on rectification and filter of the band pass limited audio signals. Various other implementations of envelope generator will be apparent to those skilled in the art, and these variations are intended to fall within the scope of the present invention. For example, the envelope extraction may be performed through windowing instead of Hilbert transformation and the averaging window width (in ms) may be kept constant across frequencies or specific to each filter band. Notably in the constant window case, the resulting output would be qualitatively similar to observed transmembrane potentials measured in the inner hair cells and/or excitatory postsynaptic potentials (EPSP) of the auditory nerve. To explain, this type of windowing would computed mathematically in the same way but would result different behavior depending on relationship between the signal's input frequency and the averaging window's duration. Two cases at opposite ends of this relationship spectra are:

a) Channels (Frequency band) with frequencies whose wavelengths are long compared to the averaging window's width, results in an output that would track (and phase lock to) their channel's carrier signal frequency, b) Channels (Frequency band) with frequencies whose wavelengths are short compared to the averaging window's width would produce an output that would track their carrier's envelope.

The device further includes a derivative unit configured to determine time based derivatives of band pass limited audio signal and/or a derived band pass limited audio signal. The derivative unit may include signal derivative techniques that are well-known in the art like Laplace derivative operator. In an embodiment, the functioning of the derivative unit may be included in the processor.

The device may further include a comparator that is configured to compare the rate of change with the predetermined criterion. The predetermined criterion is selected from a group consisting of (i) zero crossing of a time based second-order derivative of the band pass limited audio signal and/or the derived band pass limited audio signal. Therefore, the zero crossing of a time based second-order derivative determines the maximum slope, i.e when the rate of change is maximum. Typically such determination is restricted to onset time corresponding to maximum positive slope of the band pass limited audio signal and/or a derived band pass limited audio signal. However, maximum negative slope may also be used, and/or (ii) crossing of a time based first derivative of the band pass limited audio signal and/or derived band pass limited audio signal beyond a derivative threshold value. The derivative threshold value may be predetermined or be adaptively adjusted.

The rate of change based predetermined criterion allows for anticipating a quiet or loud event in advance. This facilitates either adjusting mapping of stimulation signal to target charge amounts for individual electric pulse that is delivered to the electrode and/or adjusting the stimulation level while using an unadjusted mapping to the target charge, thus ensuring that the stimulation is above the threshold level and below maximum comfortable level respectively (described later) of the user of the auditory device. This may be achieved by the processor that is configured to adjust the determined stimulation level and/or adjust the mapping of the stimulation level to the target charge amounts if the rate of change of the band pass limited audio signal and/or a derived band pass limited audio signal is below a first derivative threshold value or beyond a second derivative threshold value. In an embodiment, either the first or the second derivative threshold value may be used.

In yet another embodiment, the onset time may also be determined by level of the band pass limited signal and/or the derived band pass limited audio signal crossing a threshold level value.

In a healthy cochlea, it is generally accepted that action of the inner hair cells performs an envelope extraction process for high frequencies and for low frequencies, they instead extract the temporal fine structure. However because onset timing is useful throughout the entire frequency range, therefore, according to an embodiment, it is not necessary to make any distinction between low and high frequency regions of the cochlea. For example, in the constant window embodiment explained above, the 'envelope extraction' has already produced different outputs for the low and high frequency regions as described above but the onset timing extraction for these could be the same. Therefore, the type of onset timing extraction described here can be applied to any electrode stimulating any frequency region of the cochlea with the expectation of benefit.

In another embodiment, the processor may be adapted to determine the frequency band of the band pass limited audio signal and accordingly, determine whether the incoming band pass limited signal is to be sent to the envelope generator. If the determination results in a decision of skipping the envelope generator, then then the processor may direct the band pass limited signal directly to the derivative unit and/or signal level detector instead of to the envelope generator. Such determination by the processor may be based on a cut off frequency that defines the low frequencies and high frequencies. The low frequency is typically below 1500 Hz, and the high frequency is generally above 1500 Hz. Other frequency ranges may be used in order to define the low frequencies and high frequencies, thus defining whether the band pass limited audio signal or the derived band pass limited audio signal will be used for determining onset time. As neurons are sensitive to onsets, therefore at low frequencies, these onsets may be part of the carrier signal of band pass limited audio signal and neurons phase lock to them providing fine time structure (FTS). At high frequencies, these onsets are envelope onsets.

According to an embodiment, the processor may also be configured to apply some initial pre-processing to the input acoustic audio signal, e.g., automatic gain control, noise reduction, and other conventionally known signal processing algorithms that are employed in a speech processor of the auditory devices.

The device may further include a signal level detector that is configured to determine a stimulation level for the electrode stimulation signal in accordance with a signal level of the band pass limited audio signal and/or a derived band pass limited audio signal satisfying a predefined criterion. The signal level detector may be configured to calculate a magnitude or a magnitude squared of the band pass limited audio signal and/or a derived band pass limited audio signal in order to determine the stimulation level. Based on the determined stimulation level, the signal generator may be configured to generate the electrode stimulation signal for the electrode in accordance with the determined stimulation level.

The predefined criterion in relation to the signal detector may include the peak amplitude of the band pass limited audio signal and/or derived band pass limited audio signal. In another embodiment, the predefined criterion includes amplitude corresponding to the onset time of the band pass limited audio signal and/or a derived band pass limited audio signal. Various signal detectors, known in the art may be employed for example the signal level detection may include a peak detector.

The device further includes a pulse generator configured to generate an electric current pulse corresponding to the electrode stimulation signal. The electrode is configured to stimulate a target tissue in contact or adjacent to the electrode in accordance with the electric current pulse. The pulse generator is connected downstream to the signal generator, which provides the electrode stimulation signal. According to an embodiment, the electric current pulse includes the information about the determined onset time. According to another embodiment, the electric current pulse includes the information about the determined stimulation level. According to yet another embodiment, the electric current pulse includes information about both the onset time and stimulation level.

The pulse generator utilizes a mapping function or an enhanced mapping function. The electric current pulse including the stimulation level is based on a compressor mapping function, which defines an electric stimulation level of the electric current pulse for an electrode as a function of the determined stimulation level. The determined stimulation level on logarithmic scale are mapped directly to the electrical stimulation level. In other words, the mapping function defines how target charge amounts for individual charge pulse in each pulse stream or auditory channel of a defined audio frequency range associated with the implanted electrodes may be computed from the determined stimulation level using linear or piecewise linear mapping function. Typically, the mapping function extends linearly between a lower kneepoint and an upper kneepoint. In the lower knee point, the mapping function maps a lower threshold level $L_T$ corresponding to the user's hearing threshold into the threshold charge T. In the upper knee point, the mapping function maps a maximum comfortable level/upper threshold level $L_C$ corresponding to the user's UCL into the maximum comfortable charge C. Between the lower and upper knee points, the mapping function has a constant and positive incremental gain $G_i$ of $(C-T)/(L_C-L_T)$. However, in another embodiment, an enhanced mapping function may also be used. The enhanced mapping function deviates from the mapping function only in that it extends from the lower knee point to the upper knee point via an intermediate knee point, such that the incremental gain $G_i$ is larger between the lower knee point and the intermediate knee point than the incremental gain between the intermediate knee point and the upper knee point. At the intermediate knee point, the enhanced mapping function maps an intermediate threshold level to an intermediate charge. Compared to the mapping function, the enhanced mapping function thus applies a level expansion to audible signal levels below the intermediate threshold level and a level compression to comfortable signal levels above the intermediate threshold level. The purpose of the intermediate knee point is primarily to enhance information conveyed in speech and thus improve the user's ability to decode and understand speech.

In an embodiment, the device may further include a pulse scheduler that is adapted to prioritize which pulses get sent to the pulse generator. This may be useful in order to avoid hardware conflict. For example, such conflict may arise in scenarios when separate current sources are not used for each electrode and the current source might be busy servicing another electrode.

The pulse scheduler is configured to adapt the pulses for cochlear delays if such delay has not already been taken into account in early stages of processing. For this, the pulse scheduler may include information about the cochlear travel times for different frequency channels and their levels.

Therefore, the disclosure offers
a) the time derivative based technique that allows for determining the onset time, i.e. when the electrode to be fired,
b) the stimulation level determination and mapping technique that allows for determining the electrical stimulation level, i.e. how strongly the electrode to be fired, and
c) the frequency distribution among electrodes and placement of electrodes along the cochlea that allows for determining which electrode to be fired, i.e. which frequency region of the cochlea is to be stimulated.

In one embodiment, the auditory device comprises a cochlear implant (CI), which are surgically-implanted prosthetic devices that provide the profoundly deaf with sensations of sound. A cochlear implant typically includes an external part that sits behind the ear and a second part that is surgically placed under the skin.

The external part usually includes a) a microphone for picking up sound from the environment and generating the incoming audio signal, b) a speech processor that selects and processes sounds picked up by the microphone. The speech processor may include the filterbank, processor, envelope generator, derivative unit, comparator, signal level detector, the signal generator c) a transmitter for transmitting processed signals such as the stimulation signal from the speech processor to the implanted second part. The second part usually includes a) an implanted receiver for receiving the transmitted stimulation signal; b) an implanted stimulator (e.g. pulse generator), which converts the received stimulation signals into the electric pulses, and c) an electrode array comprising a group of electrodes implanted at specific insertion depths in the cochlea such that electrode position within the cochlea replicate place-frequency mapping of normal hearing. The electrodes collect the electric pulses corresponding to a particular frequency from the stimulator and send impulses by way of the auditory nerve to the brain, which recognizes the signals as sound. The skilled person would appreciate that possible modifications in the general CI set are possible. For example, a fully implantable CI where all components are implanted in the recipient is also possible. In this set up, a power source in the fully implantable CI may be inductively charged from outside of the CI recipient. In another example, fully implantable CI may still have the microphones in the external part in order to have better sound capturing capabilities compared to the microphones that are surgically implanted.

In an embodiment, the CI includes an implanted plurality of electrodes configured to be disposed within a cochlea of a user. Each electrode of the plurality of electrodes includes a different frequency distribution as defined by a corresponding audio frequency range. Thus, the onset time and/or stimulation level computed from the band pass limited audio signal or derived band pass limited audio signal is used to trigger the electrode that is assigned to the frequency represented by the frequency band.

The disclosed CI may include any or all the features of the disclosed auditory device.

In another embodiment, the auditory device includes a bilateral cochlear implant system (CIS). The bilateral CIS includes two implants, one in each ear i.e. a left cochlear implant (CI) and a right cochlear implant (CI). In one embodiment, the left CI and right CI includes separate speech processor. However, in another embodiment, the left CI and the right CI share a common speech processor except the microphones. In the preceding embodiments with separate and common speech processor, microphones relating to each ear are positioned at or in the vicinity of the respective ear, i.e. a left microphone receiving sound arriving at the left ear and a right microphone receiving sound arriving at the right ear. The microphone left and right incoming signals from the left microphone and the right microphone are provided to the respective speech processor. Similarly, the left CI and the right CI may also include separate or common implanted stimulator.

The left CI includes a left microphone, which provides a left incoming audio signal. Based on the technique disclosed above, the left incoming audio signal is used to determine a left onset time and/or a left stimulation level for a left band pass filtered signal and/or derived left band pass filtered signal. The left onset time and/or left stimulation level is used to generate a left electrode stimulation signal based on which a left electric current pulse is generated. The left CI further includes a left electrode array including an electrode, associated with the left band pass filtered signal and/or derived left band pass filtered signal, to which the left electric current pulse is delivered. The left electric current pulse thus stimulates a left cochlea of the user.

The right CI includes a right microphone, which provides a right incoming audio signal. Based on the technique disclosed above, the right incoming audio signal is used to determine a right onset time and/or a right stimulation level for a right band pass filtered signal and/or derived right band pass filtered signal. The right onset time and/or right stimulation level is used to generate a right electrode stimulation signal based on which a right electric current pulse is generated. The right CI further includes a right electrode array including an electrode, associated with the right band pass filtered signal and/or derived right band pass filtered signal, to which the right electric current pulse is delivered. The right electric current pulse thus stimulates a left cochlea of the user.

The left microphone and the right microphone are positioned at or in the proximity of or in the ear canal of the left ear and the right ear of the bilateral CI user respectively. The left and/or the right microphone may include multiple input microphones. It is understandable that the incoming left incoming audio signal and right incoming audio signal are typically the output signals of the left and right microphones located in the vicinity of the left and right ear, respectively.

In the disclosed bilateral CIS, the difference between the left onset time and the right onset time defines an interaural time difference (ITD). Additionally or alternatively, the difference between the left stimulation level and the right stimulation level defines an interaural level difference (ILD).

In one embodiment, the processor is configured to enhance the interaural time difference and/or the interaural level difference. For example, the ITD may be enhanced by including a further delay between the left onset time and the right onset time. Additionally or alternatively, energy may be added or subtracted between the left stimulation level and the right stimulation level in order to enhance the ILD.

The disclosed left CI and/or right CI of the bilateral CIS may include one or more features of the disclosed auditory device. For example the left onset time and/or right onset time with or without left stimulation level and/or right stimulation level may be calculated based on the disclosure in relation to the auditory device.

It is apparent, based on the disclosure the information contained in the derived band pass limited audio signal 'onsets' are used for binaural ITD and source localization. In addition, these onsets are also used to coordinate synchronized responses across the cochlea that indicate a loud event. Thus, firing of a neuron (therefore an electrode) is linked together with how loud and sudden a sound event is.

According to an embodiment, a bilateral cochlear implant system comprising a first auditory device and a second auditory device. The first auditory device and second auditory device include features of the auditory device disclosed in the description. The bilateral cochlear implant includes a left cochlear implant that includes the first auditory device, the left cochlear implant comprises a left microphone configured to provide a left incoming audio signal. The left cochlear implant is configured to determine a left onset time and/or a left stimulation level for a left band pass filtered signal and/or derived left band pass filtered signal, and to generate a left electrode stimulation signal for delivering a left electric current pulse to an electrode, associated with the left band pass filtered signal and/or derived left band pass filtered signal, of a left electrode array for stimulating a left cochlear of the user. The bilateral cochlear implant includes a right cochlear implant that includes the second auditory device. The right cochlear implant comprises a right microphone configured to provide a right incoming audio signal, the right cochlear implant. The right cochlear implant is configured to determine a right onset time and/or a right stimulation level for the right band pass filtered signal and/or the derived right band pass filtered signal, and to generate a right electrode stimulation signal for delivering a right electric current pulse to an electrode, associated with the right band pass filtered signal and/or the derived right band pass filtered signal, of a right electrode array for stimulating a right cochlea of the user.

According to another embodiment, a method for generating an electrode stimulation signal by an auditory device comprising a plurality of implanted stimulation electrodes is disclosed. The method includes filtering an incoming audio signal into a plurality of band pass limited audio signals, each band pass limited audio signal relating to an audio frequency band. The method further includes extracting an onset time for firing an electrode in accordance with rate of change of a band pass limited audio signal and/or a derived band pass limited audio signal satisfying a predetermined criterion. Lastly, the method includes generating the electrode stimulation signal for the electrode in accordance with the determined onset time.

The method further includes generating a signal envelope for the band pass limited audio signal, the signal envelope defining the derived band pass limited audio signal.

In different embodiments, the predetermined criterion is selected from a group consisting of zero crossing of a time based second-order derivative of the band pass limited audio signal and/or the derived band pass limited audio signal, and crossing of a time based first derivative of the band pass limited audio signal and/or derived band pass limited audio signal beyond a derivative threshold value.

The method may further include steps of determining a stimulation level for the electrode stimulation signal in accordance with a signal level of the band pass limited audio signal and/or a derived band pass limited audio signal satisfying a predefined criterion; and generating the electrode stimulation signal for the electrode in accordance with the determined stimulation level. The predefined criterion is selected from a group consisting of peak amplitude of the band pass limited audio signal and/or a derived band pass limited audio signal, and amplitude corresponding to the onset time of the band pass limited audio signal and/or a derived band pass limited audio signal.

Post processing, the stimulation signal is delivered to the electrode as an electric current pulse for stimulating a target tissue in contact or adjacent to the electrode.

In different embodiments, the disclosed method is implemented in a cochlear implant or a bilateral cochlear implant system. In the bilateral cochlear implant system, respective onset time and stimulation level of the left side CI and the right side CI defines the ITD and ILD, thus providing localization cues.

The disclosed method is configured to include any feature that is described above in relation to the auditory device disclosure.

BRIEF DESCRIPTION OF ACCOMPANYING FIGURES

The aspects of the disclosure may be best understood from the following detailed description taken in conjunction with the accompanying figures. The figures are schematic and simplified for clarity, and they just show details to improve the understanding of the claims, while other details are left out. The individual features of each aspect may each be combined with any or all features of the other embodiments. These and other embodiments, features and/or technical effect will be apparent from and elucidated with reference to the illustrations described hereinafter in which:

DETAILED DESCRIPTION

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, steps, processes, etc. (collectively referred to as "elements").

Figure 1:
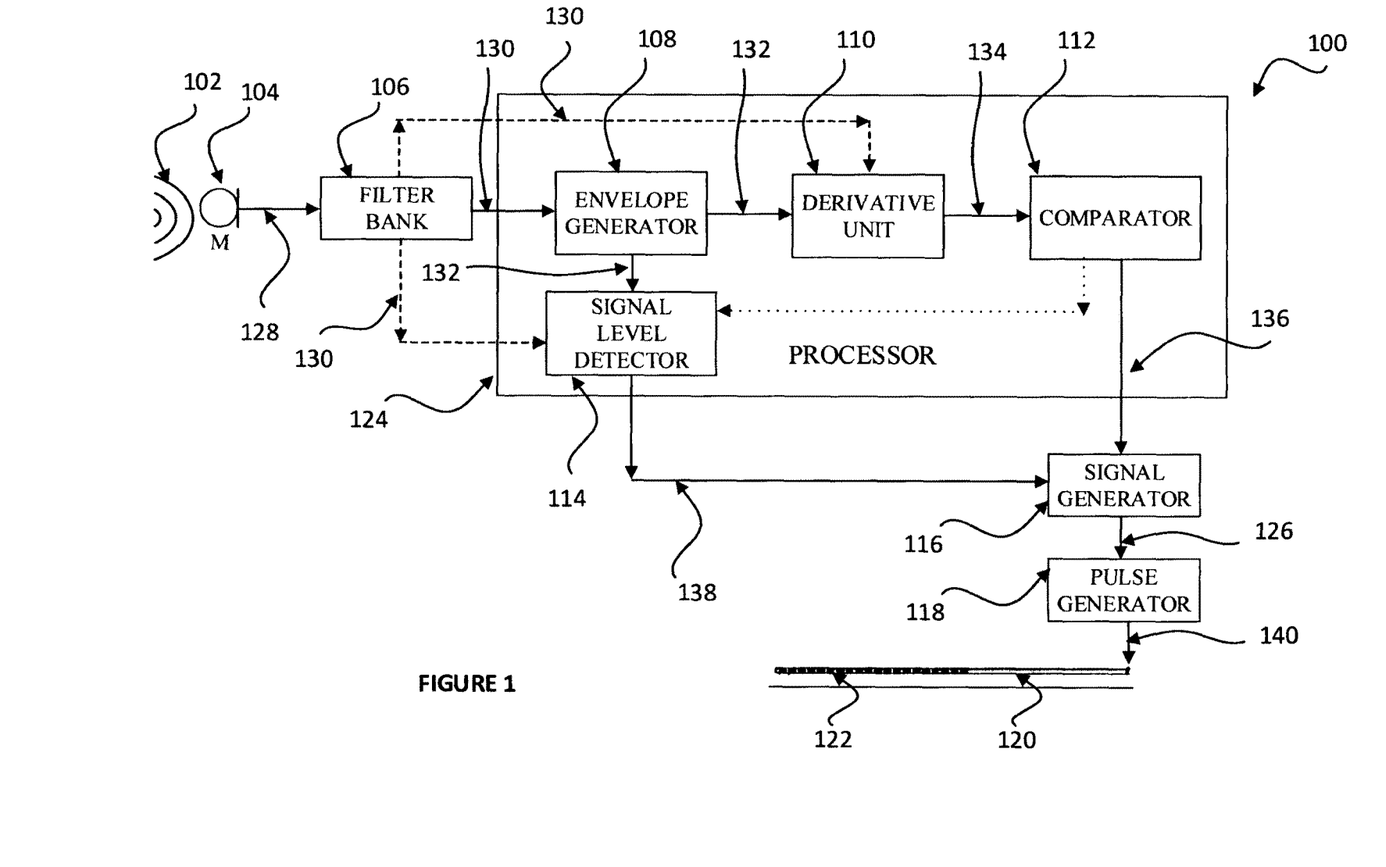
FIG. 1 illustrates a schematic representation of the auditory device according to an embodiment of the disclosure.

FIG. 1 illustrates a schematic representation of the auditory device 100 according to an embodiment of the disclosure. The auditory device 100 comprises a plurality of implanted stimulation electrodes 122 for generating an electrode stimulation signal 126 is disclosed. The device includes a filter bank 106 configured to filter an incoming audio signal 128 into a plurality of band pass limited audio signals 130, each band pass limited audio signal relating to an audio frequency band. Although the figure shows only one output from the filterbank but it is understandable that the output includes a plurality of band limited audio signals as defined by the audio frequency bands associated with the filters in the filterbank 106. The device further includes a processor 124 configured to extract an onset time 136 for firing an electrode 122 in accordance with rate of change of a band pass limited audio signal 130 and/or a derived band pass limited audio signal 132 satisfying a predetermined criterion, and a signal generator 116 for generating the electrode stimulation signal 126 for the electrode 122 in accordance with the determined onset time.

In an embodiment, the device 100 includes a microphone 104 that is adapted to receive the sound signals 102 from user's environment. The microphone is configured to generate the incoming audio signal 128 based on the received sound signal 102.

The device may include an envelope generator 108 receiving the band pass limited audio signal 130 and configured to generate a signal envelope 132 for the band pass limited audio signal 130, the signal envelope 132 defining the derived band pass limited audio signal. The device may further include a derivative unit 110 receiving the band pass limited audio signal 130 (representative broken line) and/or derived band pass limited audio signal 132 (representative solid line) from the filter bank and envelope generator respectively. The derivative unit is configured to determine time based derivatives of band pass limited audio signal and/or a derived band pass limited audio signal. The device may also include a comparator 110 that receives the derivative values 134 from the derivative unit 110. The comparator is configured to compare the rate of change with the predetermined criterion. The predetermined criterion is selected from a group consisting of zero crossing of a time based second-order derivative of the band pass limited audio signal and/or the derived band pass limited audio signal, and crossing of a time based first derivative of the band pass limited audio signal and/or derived band pass limited audio signal beyond a derivative threshold value.

Based on the determined onset time information 136, the signal generator 116 may be configured to generate the electrode stimulation signal 126 comprising the onset time information for the electrode associated with the processed band pass limited audio signal and/or derived band pass limited audio signal. The device further includes a pulse generator 118 (typically implanted) that receives the electrode stimulation signal 126. The pulse generator is configured to generate an electric current pulse 140, with onset time information incorporated therein, corresponding to the electrode stimulation signal. The generated electric current pulse is delivered to the electrode 122 (usually part of an implanted electrode array 120) associated with the processed band pass limited audio signal 130 and/or derived band pass limited audio signal. The electrode then stimulates, with the received electric pulse, a target tissue in contact or adjacent to the electrode 122. Thus, the disclosed time derivative based technique allows for determining the onset time, i.e. when the electrode is to be fired.

In another embodiment, the device may further include a signal level detector 114, which receives the band pass limited audio signal 130 (representative broken line) and/or derived band pass limited audio signal 132 (representative solid line) from the filter bank and envelope generator respectively. The signal level detector is configured to determine a stimulation level 138 for the electrode stimulation signal 126 in accordance with a signal level of the band pass limited audio signal 130 and/or a derived band pass limited audio signal 132 satisfying a predefined criterion. The predefined criterion may be selected from one of the peak amplitude of the band pass limited audio signal and/or a derived band pass limited audio signal, and amplitude corresponding to the onset time of the band pass limited audio signal and/or a derived band pass limited audio signal. For the latter embodiment where the amplitude corresponding to the onset time determines the stimulation level, the onset time information is provided (representative dotted line) from the comparator 112 to the signal level detector 114.

Based on the determined stimulation level information 138, the signal generator 116 may be configured to generate the electrode stimulation signal 126 comprising the determined stimulation level for the electrode associated with the processed band pass limited audio signal and/or derived band pass limited audio signal. The device further includes a pulse generator 118 (typically implanted) that receives the electrode stimulation signal 126. The pulse generator is configured to generate an electric current pulse 140, with the stimulation level information incorporated therein, corresponding to the electrode stimulation signal. The generated electric current pulse is delivered to the electrode 122 (usually part of an implanted electrode array 120) associated with the processed band pass limited audio signal 130 and/or derived band pass limited audio signal. The electrode then stimulates, with the received electric pulse, a target tissue in contact or adjacent to the electrode 122.

Figure 2:
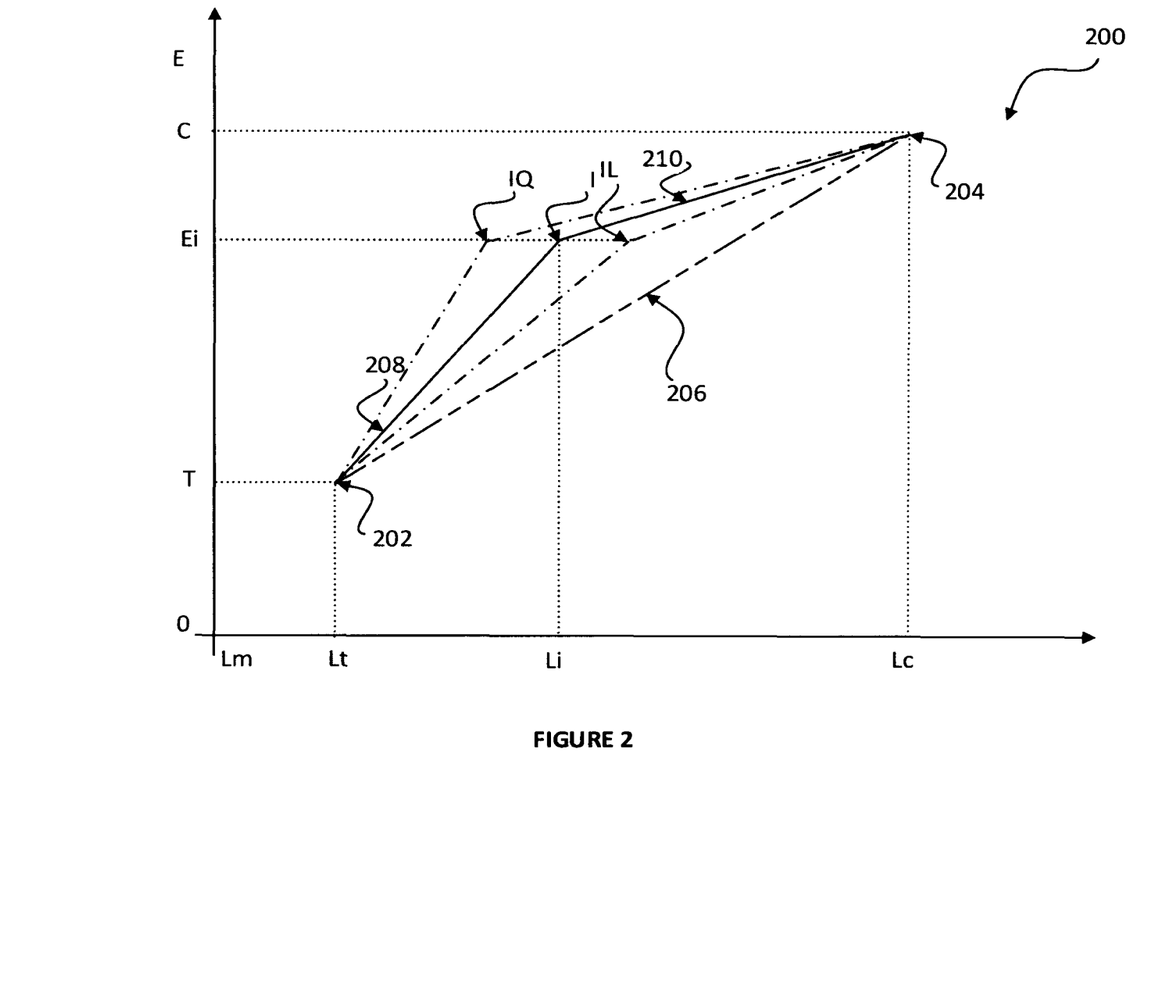
FIG. 2 illustrates mapping functions according to different embodiments of the disclosure.

The pulse generator 118 typically utilizes a mapping function or an enhanced mapping function, which defines an electric stimulation level of the electric current pulse for an electrode as a function of the determined stimulation level. FIG. 2 illustrates mapping functions according to different embodiments of the disclosure. The mapping functions (200) defines how target charge amounts E for individual charge pulse in auditory channel of a defined audio frequency range associated with the implanted electrodes may be computed from the determined stimulation level L. At the lower knee point 202, the mapping function maps a lower threshold level $L_T$ corresponding to the user's hearing threshold into the threshold charge T. At the upper knee point 204, the mapping function maps a maximum comfortable level/upper threshold level $L_C$ corresponding to the user's UCL into the maximum comfortable charge C. In one embodiment, between the lower and upper knee points, the mapping function 206 (broken line) has a constant and positive incremental gain $G_i$ of $(C-T)/(L_C-L_T)$. However, in another embodiment, an enhanced mapping function (208-210, solid line) extends from the lower knee point to the upper knee point via an intermediate knee point I, such that the incremental gain $G_i$ is larger between the lower knee point and the intermediate knee point than the incremental gain between the intermediate knee point and the upper knee point. At the intermediate knee point, the enhanced mapping function maps an intermediate threshold level to an intermediate charge Ei.

In an embodiment, for a specific frequency band, the intermediate kneepoint I for the enhanced mapping function may be adjusted in response to whether a sudden loud or quiet event is anticipated. For example, for quiet anticipated event, the intermediate threshold level is adjusted to IQ such that soft incoming audio signal receives higher incremental gain between the lower threshold level Lc and intermediate threshold level IS in comparison to that between the lower threshold level Lc and intermediate threshold level I. In another example of loud anticipated event, the intermediate threshold level is adjusted to IL such that loud incoming audio signal receives lower incremental gain between the lower threshold level Lc and intermediate threshold level IQ in comparison to that between the lower threshold level Lc and intermediate threshold level I. The anticipated quiet or loud event is determined based on the rate of the change of the band pass limited audio signal and/or derived band pass limited audio signal, i.e. the derivative value is below a first derivative value or the derivative value is beyond a second derivative value.

Thus, the stimulation level determination and mapping technique allows for determining the electrical stimulation level, i.e. how strongly the electrode should be fired.

The determination whether the band pass limited audio signal or the derived band pass limited audio signal be used is a function of the frequency band being processed by the disclosed auditory device. In general, the band pass limited audio signal is used for low frequencies, whereas the derived band pass limited audio signal is used for high frequencies. The processor 124 may be configured to determine, based on the cut off frequency, whether the frequency band of the bandpass limited audio signal 130 under analysis represents low or high frequency. Based on such determination, the band pass limited audio signal 130 may be directed either to the envelope generator 108 for generation of signal envelope 132 or directly to the derivative unit 110 and/or signal level detector 114.

The processor 124 may be configured to include the functionalities one or more functional units such as the envelope generator 108, derivative unit 110, comparator 112, and signal level detector 114. The processor may also include the functionality of the signal generator 116. The processor may be comprised in a speech processor unit (not shown) of the auditory device. The speech comprised in a speech processor unit may further include the microphone 102 and the fitlerbank 104.

Figure 3A:
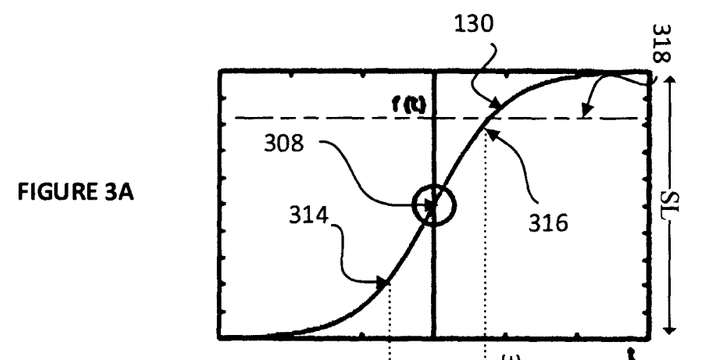
FIG. 3A illustrates a section of the band pass limited audio signal according to an embodiment of the disclosure.
Figure 3B:
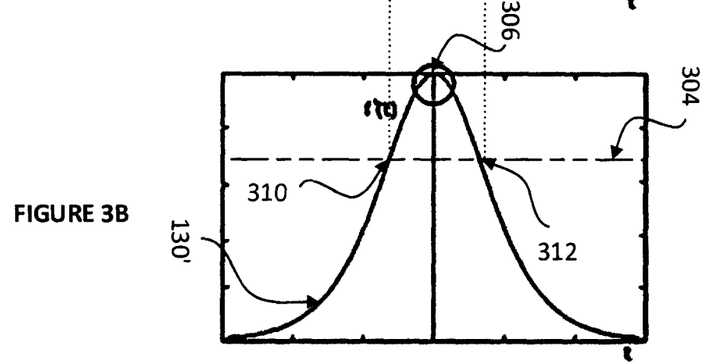
FIG. 3B illustrates a first derivative of the section of the band pass limited audio signal according to an embodiment of the disclosure.
Figure 3C:
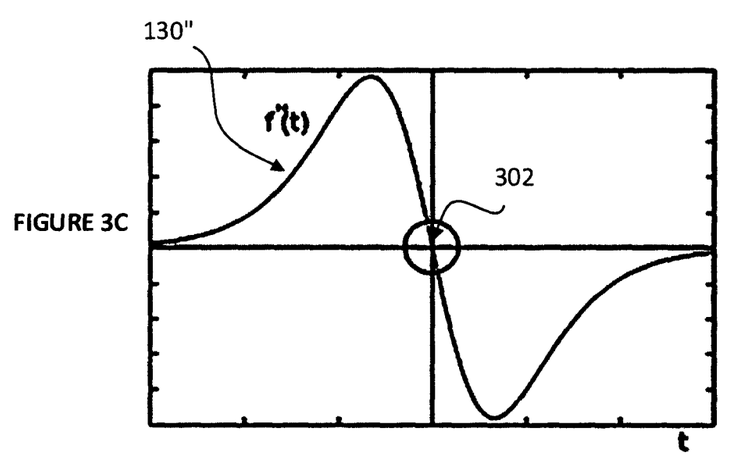
FIG. 3C illustrates a section of second derivative of the section of the band pass limited audio signal according to an embodiment of the disclosure.

FIG. 3A illustrates a section of the band pass limited audio signal 132 according to an embodiment of the disclosure. FIG. 3B illustrates a first derivative 132' of the section of the band pass limited audio signal according to an embodiment of the disclosure. FIG. 3C illustrates a section of second derivative 132" of the section of the band pass limited audio signal according to an embodiment of the disclosure. The figures are shown in relation to the band pass limited audio signal 130, however the disclosed principle is also applicable on the derived band pass limited audio signal 132.

In one embodiment, the FIG. 3C shows the zero crossing 302 of a time based second-order derivative of the band pass limited audio signal 132. The zero crossing 302 of the time based second-order derivative 132" determines the maximum slope as represented by 306 in FIG. 3B. The maximum slope corresponds to the point 308 in the band pass limited audio signal, and this point 308 determines the onset time for firing the electrode. In another embodiment, referring to FIG. 3B, the crossing (310 or 312) of a time based first derivative 130' of the band pass limited audio signal 130 beyond a derivative threshold value 304 determines the onset time (314 or 316).

In yet another embodiment, the onset time may also be determined by level of the band pass limited signal crossing a threshold level value 318.

In an embodiment, the stimulation level is the peak amplitude SL of the band pass limited audio signal. In another embodiment, the stimulation level includes amplitude (relating to points 314 or 316) corresponding to the onset time (314 or 316) of the band pass limited audio signal.

Figure 4:
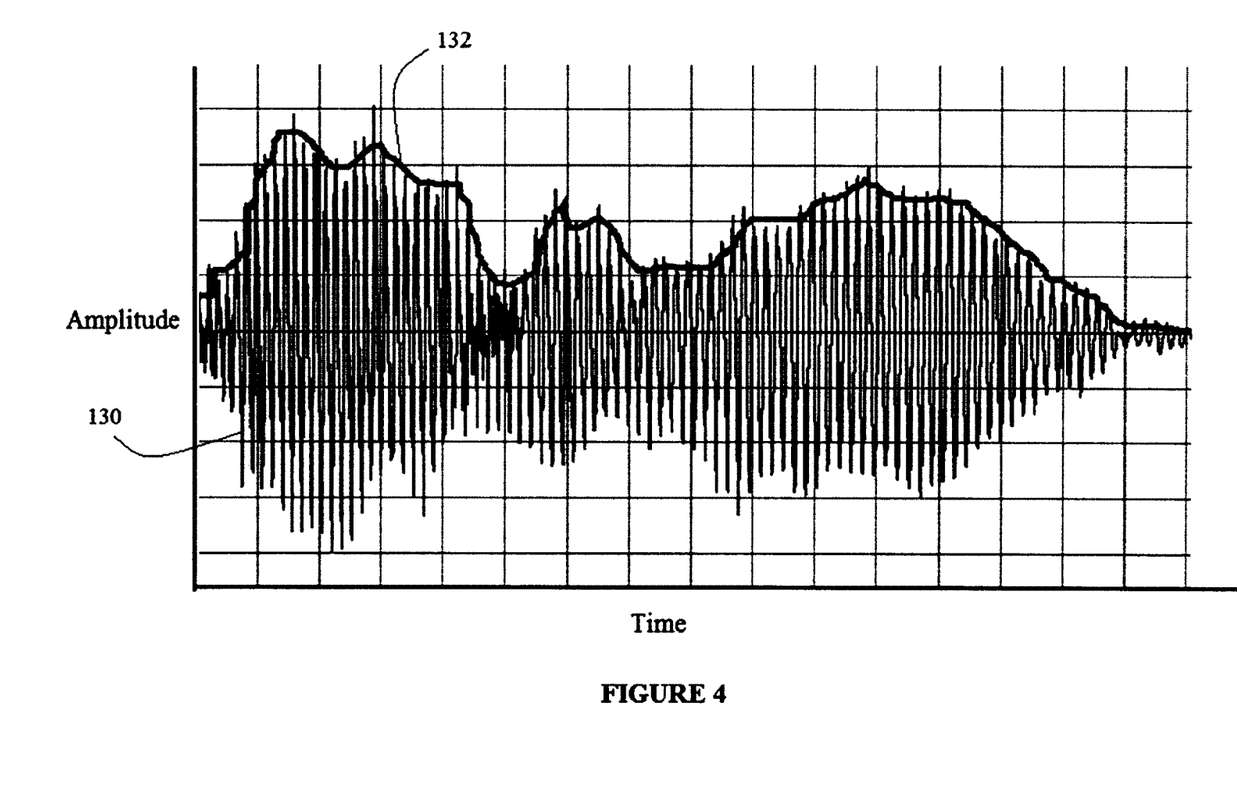
FIG. 4 illustrates a band pass limited audio signal and a derived band pass limited audio signal according to an embodiment for the disclosure.

FIG. 4 illustrates a band pass limited audio signal 130 and a derived band pass limited audio signal 132 according to an embodiment for the disclosure. The band pass limited signal 130 is an output of one of the band pass filters of the filter bank. The one of the band pass filter includes a lower corner frequency, for example 325 Hz and an upper corner frequency, for example 490 Hz that defines the frequency band for the band pass filter. The derived band pass limited audio signal 132 is an output of the envelope generator (108, Ref. FIG. 1).

Figure 5A:
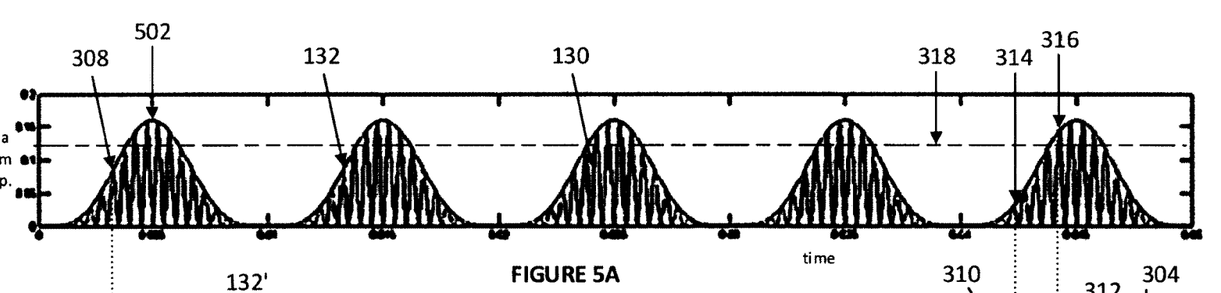
FIG. 5A illustrates a band pass limited audio signal squared and a derived band pass limited audio signal according to an embodiment of the disclosure.
Figure 5B:
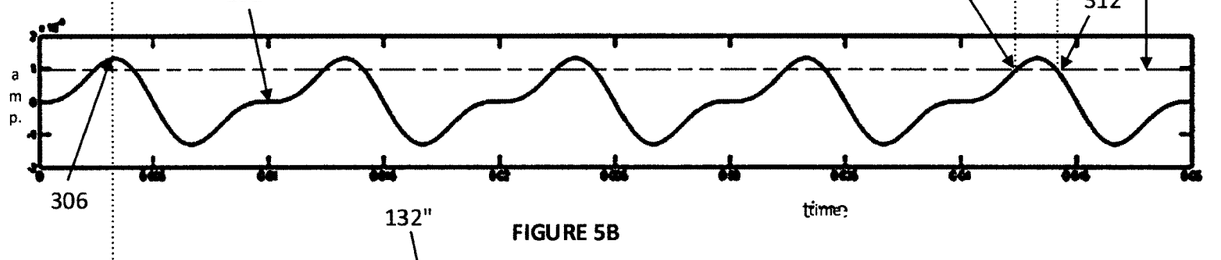
FIG. 5B illustrates a first derivative of the derived band pass limited audio signal according to an embodiment of the disclosure.
Figure 5C:
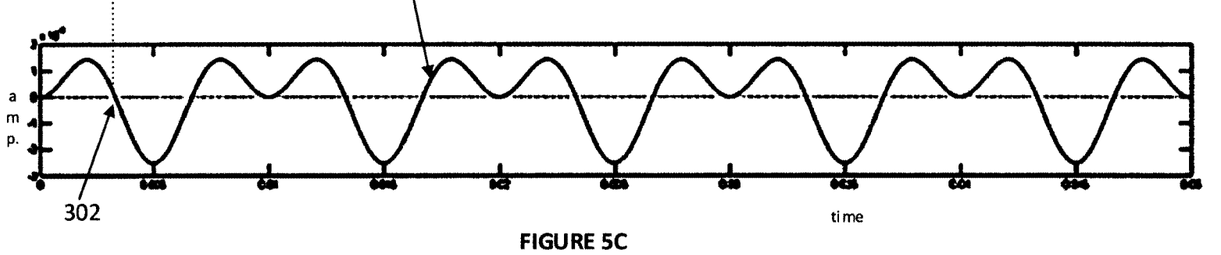
FIG. 5C illustrates a second derivative of the derived band pass limited audio signal according to an embodiment of the disclosure.

In principle, FIG. 5 illustrates a signal based representation of the section of signal based description of FIG. 3. Furthermore, FIG. 5 description is in relation to the derived band pass limited audio signal but the description is equally applicable on the band pass limited signal.

FIG. 5A illustrates a band pass limited audio signal 130 squared and a derived band pass limited audio signal 132 according to an embodiment of the disclosure. The derived band pass limited audio signal being the signal envelope corresponding to the band pass limited signal. FIG. 5B illustrates a first derivative 132' of the derived band pass limited audio signal according to an embodiment of the disclosure. FIG. 5C illustrates a second derivative 132" of the derived band pass limited audio signal according to an embodiment of the disclosure.

FIG. 5C shows zero crossing 302, determining onset time, of a time based second-order derivative of the derived band pass limited audio signal 132. The zero crossing 302 of the time based second-order derivative 130" determines the maximum slope as represented by 306 in FIG. 5B. The maximum slope corresponds to the point 308 in the derived band pass limited audio signal, and this point 308 determines the onset time for firing the electrode. In another embodiment, referring to FIG. 3B, the crossing (310 or 312) of a time based first derivative 130' of the derived band pass limited audio signal 132 beyond a derivative threshold value 304 determines the onset time (314 or 316).

In yet another embodiment, the onset time may also be determined by level of the band pass limited signal crossing a threshold level value 318.

In an embodiment, the stimulation level is the peak amplitude (corresponding to 502) of the band pass limited audio signal. In another embodiment, the stimulation level includes amplitude (relating to points 314 or 316) corresponding to the onset time (314 or 316) of the band pass limited audio signal.

In an embodiment, the auditory device comprises a bilateral cochlear implant system. The bilateral cochlear implant comprises a left cochlear implant comprising features of the auditory device disclosed in the description. The left cochlear implant also includes a left microphone configured to provide a left incoming audio signal, the left cochlear implant is configured to determine a left onset time and/or a left stimulation level for a left band pass filtered signal and/or derived left band pass filtered signal, and to generate a left electrode stimulation signal for delivering a left electric current pulse to an electrode, associated with the left band pass filtered signal and/or derived left band pass filtered signal, of a left electrode array for stimulating a left cochlear of the user. The bilateral cochlear implant system includes a right cochlear implant comprising features of the auditory device disclosed in the description. The right cochlear implant includes a right microphone configured to provide a right incoming audio signal, the right cochlear implant is configured to determine a right onset time and/or a right stimulation level for the right band pass filtered signal and/or the derived right band pass filtered signal, and to generate a right electrode stimulation signal for delivering a right electric current pulse to an electrode, associated with the right band pass filtered signal and/or the derived right band pass filtered signal, of a right electrode array for stimulating a right cochlea of the user.

Figure 6:
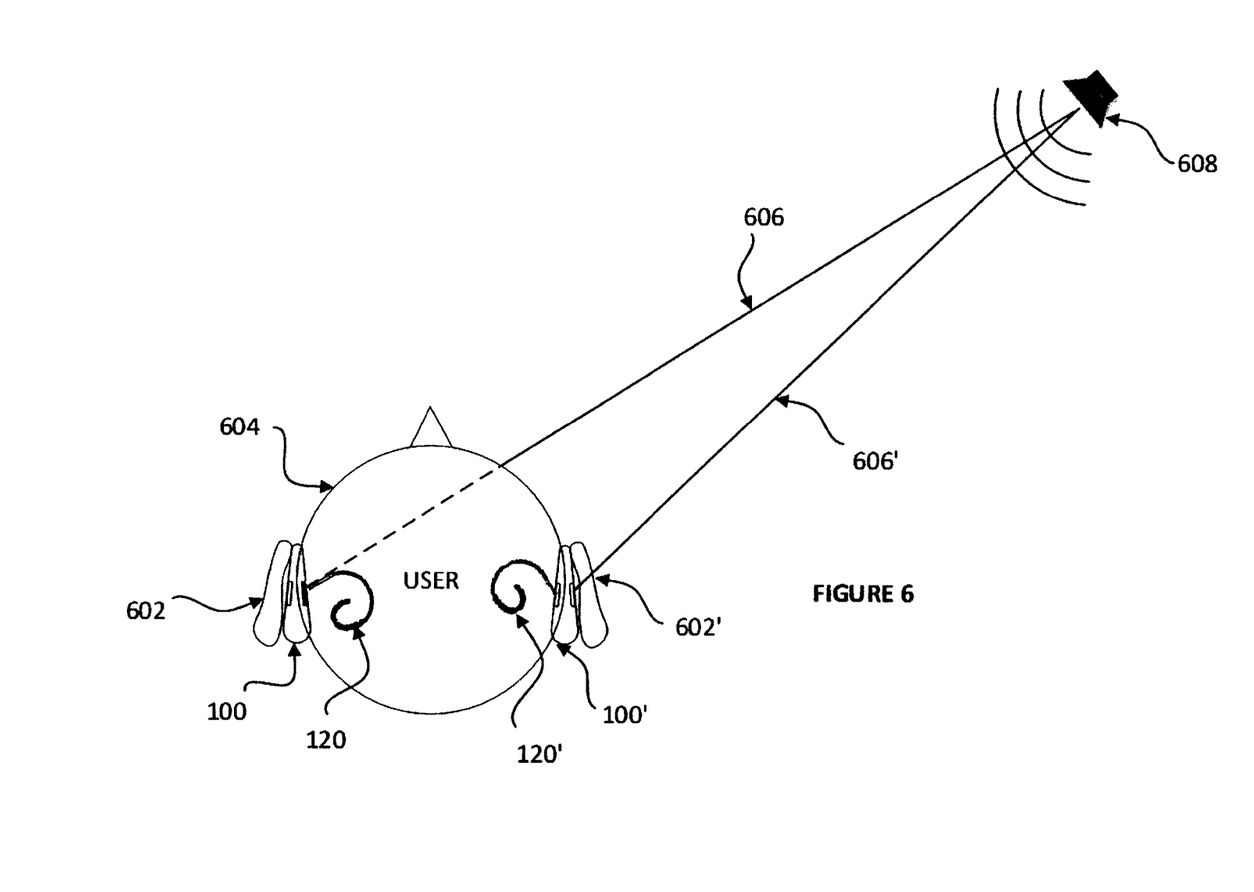
FIG. 6 illustrates a user with a bilateral cochlear implant system according to an embodiment of the disclosure.

FIG. 6 illustrates a user with a bilateral cochlear implant system according to an embodiment of the disclosure. In the illustrative scenario, the user 604 wears a bilateral cochlear implant system (100-100') comprising a left cochlear implant 100 and a right cochlear implant 100' with a left external part position at/in the vicinity of a left ear 602 and a right external part at/in the vicinity of a right ear 602' respectively. If the sound source 608 is positioned at spatial relationships with respect to the left CI and the right CI, then the sound received 606 at a left microphone of the left CI 100 and the sound received 606' at a right microphone of the right CI 100' are different in characteristics such as in terms of arrival time and amplitude. This leads to a difference between the left incoming audio signal and the right incoming audio signal, as generated by the left microphone and the right microphone. Applying the above disclosed technique in relation to the auditory device, a left onset time and a right onset time for electrodes of the left electrode array 120 and electrode of the right electrode array 120' may be estimated. The determined left and right onset times are used generate a left and right stimulation signal based on which a left electric pulse for the left electrode array and a right electric pulse for the right electrode array may be generated. For a specific frequency band, the difference between the left onset time and right onset time represents the interaual time difference.

Additionally or alternatively, the left stimulation level and the right stimulation level may also be estimated using the technique disclosed above in relation to the auditory device. The determined left and right stimulation level is used to generate the left stimulation signal and the right stimulation signal based on which a left electric pulse for the left electrode array and a right electric pulse for the right electrode array may be generated. The difference between the left stimulation level and the right stimulation level allows for determining the interaural level difference.

In one embodiment, the determined ITD or the ILD may also be enhanced to provide an improved perception of localization cues.

Figure 7:
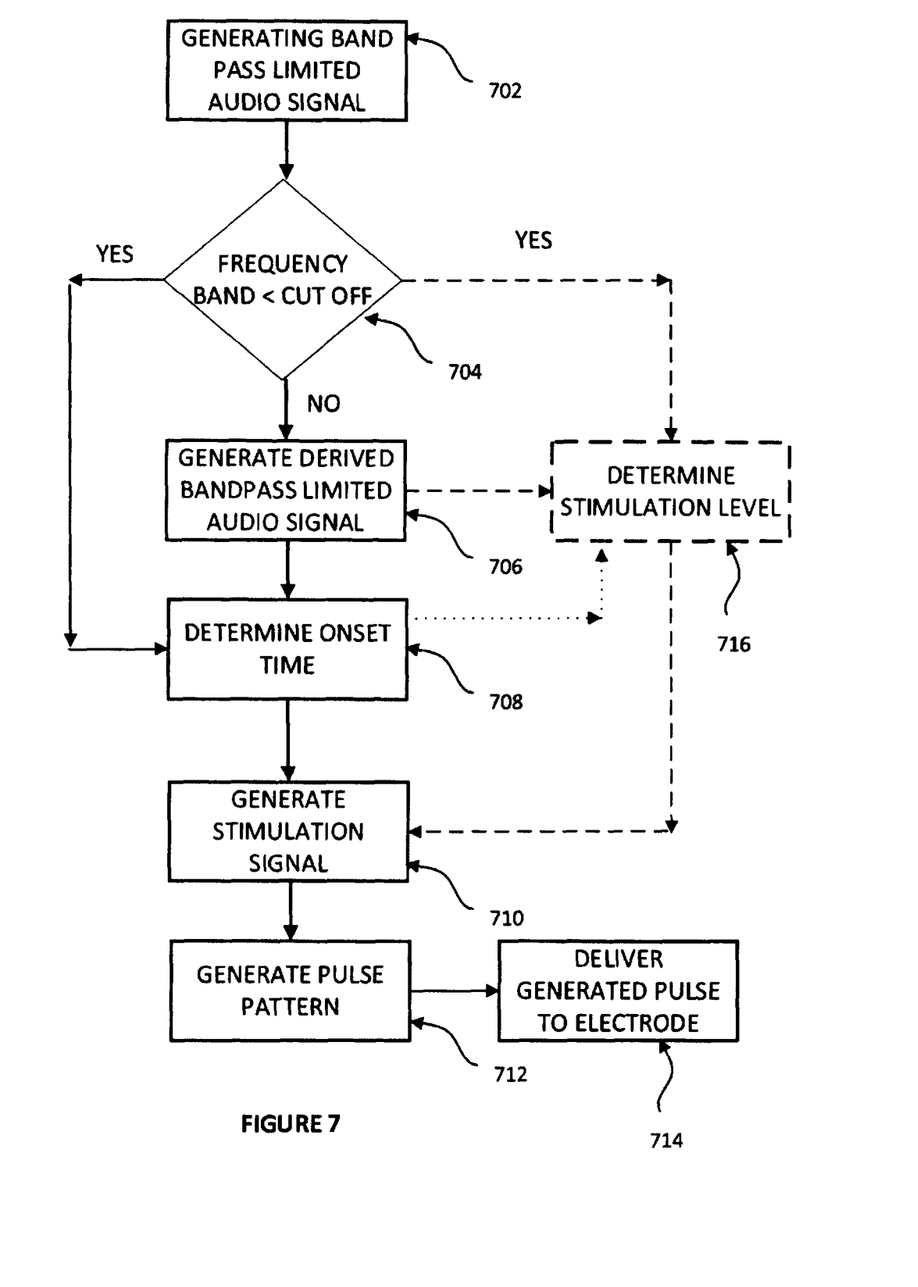
FIG. 7 illustrates methods according to different embodiments of the disclosure.

FIG. 7 illustrates methods for generating electrode stimulation signals by an auditory device according to different embodiments of the disclosure.

In one embodiment, at 702, an incoming audio signal is filtered into a plurality of band pass limited audio signals where each band pass limited audio signal relates to an audio frequency band. At 704, a determination is made whether the band pass limited audio signal for which the stimulation signal is to be generated is below a cut off frequency. The cut off defines whether the band pass limited audio signal or a derived band pass limited audio signal will be used for determining onset time and/or stimulation level. It is understandable that the determination can be reversed, i.e. whether the analyzed frequency band is above the cut off frequency. In either implementation, the disclosure relies on generating at 706 derived band pass limited audio signal for signals having a frequency band that is above the cut off frequency. At 708, an onset time is determined for the band pass limited audio signal or derived band pass limited audio signal. The determination of onset time is based on the rate of change of the band pass limited audio signal and/or the derived band pass limited audio signal satisfying a predetermined criterion. Based on the determined onset time, defining when the electrode associated with the frequency band is to be fired, a stimulation signal is generated at 710. The generated stimulation signal forms the basis for generating a pulse patter at 712, which is then delivered to the associated implanted electrode at 714. The electrode then stimulates a target tissue in contact or adjacent to the electrode.

Additionally or alternatively, in another embodiment (illustrated by the broken lines in FIG. 7), depending upon the frequency band of the analysed band pass limited audio signal, stimulation level is determined for the band pass limited audio signal or the derived band pass limited audio signal at 716. The stimulation level is determined based on a predefined criterion. The determined stimulation level is then used at 710 to generate a stimulation signal, based on which a pulse pattern at 712 is generated. The generated pulse pattern is then delivered at 714 to the electrode that is associated with the analyzed frequency band. The electrode then stimulates a target tissue in contact or adjacent to the electrode.

The predefined criterion is selected from a group consisting of peak amplitude of the band pass limited audio signal and/or a corresponding derived band pass limited audio signal, and amplitude corresponding to the onset time of the band pass limited audio signal and/or a corresponding derived band pass limited audio signal. For the latter embodiment, the determined onset time information from 708 step is provided to the step 716 (as represented by dotted line).

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, steps, operations, elements, and/or components, but do not preclude the presence or addition of one or more other features, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

We claim:

1. An auditory device for generating an electrode stimulation signal, the device comprising
   a filter bank configured to filter an incoming audio signal into a plurality of band pass limited audio signals, each band pass limited audio signal relating to an audio frequency band;
   a processor configured to extract an onset time for firing an electrode in accordance with a peak rate of change of a band pass limited audio signal and/or a derived band pass limited audio signal, said processor detecting the peak rate of change by
     generating a time based second order derivative of the band pass limited audio signal and/or derived band pass limited audio signal, and
     determining a zero crossing of the time based second-order derivative of the band pass limited audio signal and/or derived band pass limited audio signal, the zero crossing representing occurrence of the peak rate of change;
   a signal generator for generating the electrode stimulation signal for the electrode corresponding to the band pass limited audio signal and/or derived band pass limited audio signal in accordance with the onset time; and
   a plurality of implantable stimulation electrodes configured to deliver the electrode stimulation signal to a region of cochlea.

2. The device according to claim 1, further comprising an envelope generator configured to generate a signal envelope for the band pass limited audio signal, the signal envelope defining the derived band pass limited audio signal.

3. The device according to claim 1, further comprising a derivative unit configured to determine time based derivatives of band pass limited audio signal and/or a derived band pass limited audio signal.

4. The device according to claim 1, further comprising a comparator configured to compare the rate of change with the zero crossing of the time based second-order derivative of the band pass limited audio signal and/or the derived band pass limited audio signal.

5. The device according to claim 4, wherein the zero crossing corresponds to the maximum positive slope of the band pass limited audio signal and/or a derived band pass limited audio signal.

6. The device according to claim 4, wherein the zero crossing corresponds to the maximum negative slope of the band pass limited audio signal and/or a derived band pass limited audio signal.

7. The device according to claim 1, further comprising a signal level detector configured to determine a stimulation level for the electrode stimulation signal in accordance with a signal level of the band pass limited audio signal and/or a derived band pass limited audio signal satisfying a predefined criterion; and the signal generator configured to generate the electrode stimulation signal for the electrode in accordance with the stimulation level.

8. The device according to claim 7, wherein the predefined criterion is selected from a group consisting of
   peak amplitude of the band pass limited audio signal and/or a corresponding derived band pass limited audio signal, and
   amplitude corresponding to the onset time of the band pass limited audio signal and/or a corresponding derived band pass limited audio signal.

9. The device according to claim 1, further comprising a pulse generator configured to generate an electric current pulse corresponding to the electrode stimulation signal, and the electrode being configured to stimulate a target tissue in contact or adjacent to the electrode in accordance with the electric current pulse.

10. The device according to claim 1, wherein the auditory device comprises a cochlear implant comprising an implantable plurality of electrodes configured to be disposed within a cochlea of a user, each electrode of the plurality of electrodes comprising a different frequency distribution as defined by a corresponding audio frequency range.

11. A bilateral cochlear implant system comprising a first auditory device and a second auditory device according to claim 1,
    a left cochlear implant comprising the first auditory device, the left cochlear implant comprises a left microphone configured to provide a left incoming audio signal, the left cochlear implant is configured
    to determine a left onset time and/or a left stimulation level for a left band pass filtered signal and/or derived left band pass filtered signal, and
    to generate a left electrode stimulation signal for delivering a left electric current pulse to an electrode, associated with the left band pass filtered signal and/or derived left band pass filtered signal, of a left electrode array for stimulating a left cochlear of the user; and
    a right cochlear implant comprising the second auditory device, the right cochlear implant comprises a right microphone configured to provide a right incoming audio signal, the right cochlear implant is configured
    to determine a right onset time and/or a right stimulation level for the right band pass filtered signal and/or the derived right band pass filtered signal, and
    to generate a right electrode stimulation signal for delivering a right electric current pulse to an electrode, associated with the right band pass filtered signal and/or the derived right band pass filtered signal, of a right electrode array for stimulating a right cochlea of the user.

12. The device according to claim 11, wherein the processor is configured to
    enhance the difference between the left onset time and the right onset time, defining an interaural time difference; and/or
    enhance the difference between the left stimulation level and the right stimulation level, defining an interaural level difference.

13. The device according to claim 11, wherein the processor is configured to adjust the determined stimulation level or adjust mapping of the stimulation level to target charge amounts if the rate of change of the band pass limited audio signal and/or a derived band pass limited audio signal is below a first derivative threshold value or beyond a second derivative threshold value.

14. A method for generating an electrode stimulation signal by an auditory device comprising a plurality of implanted stimulation electrodes, the method comprising
   filtering an incoming audio signal into a plurality of band pass limited audio signals, each band pass limited audio signal relating to an audio frequency band;
   extracting an onset time for firing an electrode in accordance with a peak rate of change of a band pass limited audio signal and/or a derived band pass limited audio signal, wherein the peak rate of change is detected by
      generating a time based second order derivative of the band pass limited audio signal and/or derived band pass limited audio signal, and
      determining a zero crossing of the time based second-order derivative of the band pass limited audio signal and/or derived band pass limited audio signal, the zero crossing representing occurrence of the peak rate of change; and
   generating the electrode stimulation signal for the electrode corresponding to the band pass limited audio signal and/or derived band pass limited audio signal in accordance with the determined onset time.

15. The method according to claim 14, further comprising generating a signal envelope for the band pass limited audio signal, the signal envelope defining the derived band pass limited audio signal.

16. The method according to claim 14, further comprising comparing the rate of change with the zero crossing of the time based second-order derivative of the band pass limited audio signal and/or the derived band pass limited audio signal.

17. The method according to claim 16, wherein the zero crossing corresponds to the maximum positive slope of the band pass limited audio signal and/or a derived band pass limited audio signal.

18. The method according to claim 16, wherein the zero crossing corresponds to the maximum negative slope of the band pass limited audio signal and/or a derived band pass limited audio signal.

* * * * *